United States Patent [19]

Kleiner

[11] Patent Number: 5,895,352

[45] Date of Patent: Apr. 20, 1999

[54] SURGICAL RETRACTOR

[76] Inventor: Jeffrey B. Kleiner, 215 Locust La., Denver, Colo. 80220

[21] Appl. No.: 09/042,882

[22] Filed: Mar. 17, 1998

[51] Int. Cl.$^6$ ..................................................... A61B 17/02
[52] U.S. Cl. ...................... 600/206; 600/209; 600/215
[58] Field of Search ........................ 600/215, 209, 600/206, 207, 210, 211, 216, 217

[56] References Cited

U.S. PATENT DOCUMENTS

| | | | |
|---|---|---|---|
| 4,064,873 | 12/1977 | Swenson | 600/215 |
| 4,190,042 | 2/1980 | Sinnreich | 600/206 |
| 4,428,746 | 1/1984 | Mender | 600/209 |
| 4,517,965 | 5/1985 | Ellison | 600/217 |
| 4,874,375 | 10/1989 | Ellison | 604/164 |
| 5,064,428 | 11/1991 | Cope et al. | 606/127 |
| 5,067,957 | 11/1991 | Jervis | 606/108 |
| 5,080,088 | 1/1992 | LeVahn | 600/206 |
| 5,103,804 | 4/1992 | Abele et al. | 128/4 |
| 5,123,906 | 6/1992 | Kelman | 606/107 |
| 5,197,971 | 3/1993 | Bonutti | 606/192 |
| 5,290,292 | 3/1994 | Householder | 600/209 |
| 5,337,736 | 8/1994 | Reddy | 128/20 |
| 5,381,788 | 1/1995 | Matula et al. | 128/20 |
| 5,439,476 | 8/1995 | Frantzides | 600/207 |
| 5,486,183 | 1/1996 | Middleman et al. | 606/127 |
| 5,501,654 | 3/1996 | Failla et al. | 600/204 |
| 5,512,037 | 4/1996 | Russell et al | 600/206 |
| 5,607,446 | 3/1997 | Beehler et al. | 600/206 |
| 5,690,606 | 11/1997 | Slotman | 600/206 |

*Primary Examiner*—Paul J. Hirsch
*Attorney, Agent, or Firm*—Sheridan Ross P.C.

[57] ABSTRACT

A medical retractor apparatus that includes a housing assembly and a retractor assembly is provided. The housing assembly includes a retractor body having a proximal end. The retractor assembly includes a retractor element having a tip. The retractor element is extended/retracted relative to the proximal end. The retractor element is extended offset from the center of the proximal end. A guide member with a slot located at the proximal end prevents unacceptable turning of the retractor element. Preferably, the retractor element includes two spaced loops that can be surrounded by a cover member. The retractor element desirably positions a body vessel of at least about 1 cm in diameter during a surgical procedure. The retractor element has sufficient tensile and compressive strengths to position the great vessel, while avoiding unwanted bulging of the great vessel and visual interference during the surgical procedure.

16 Claims, 5 Drawing Sheets

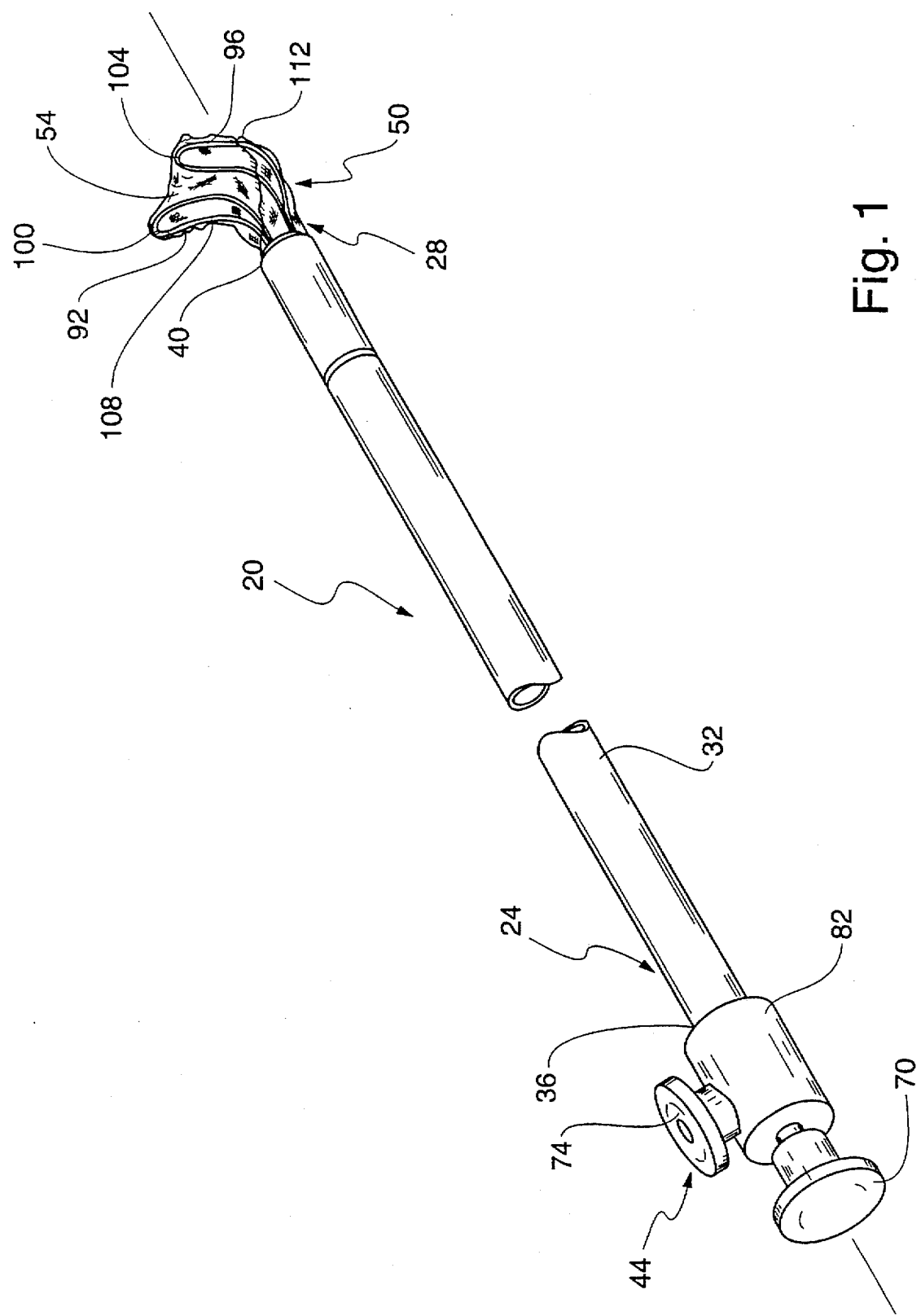

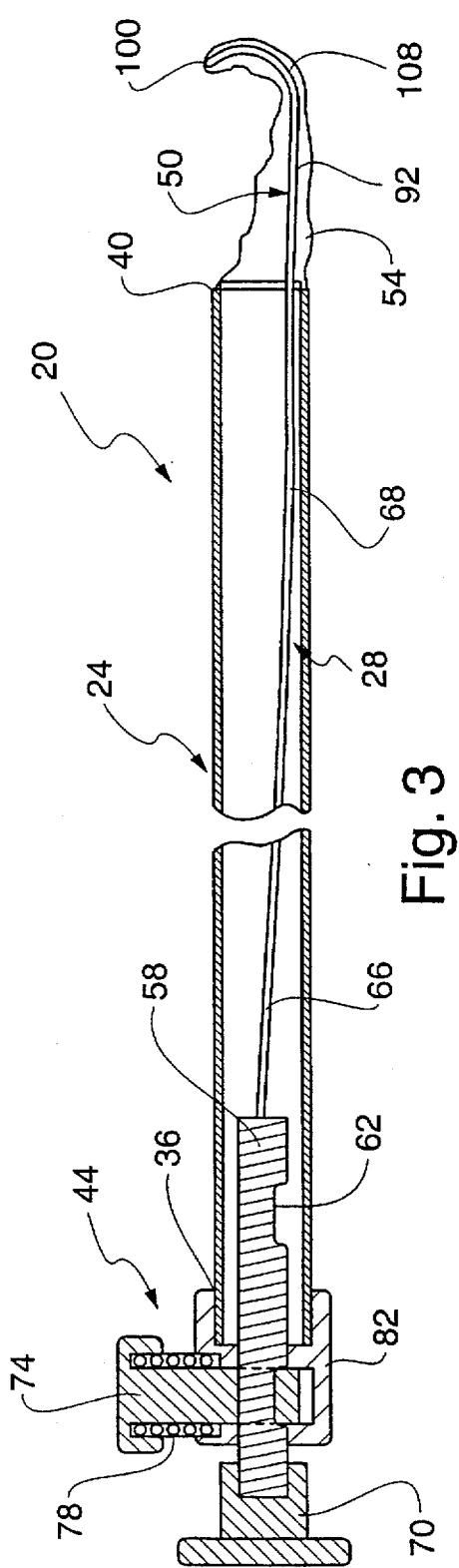
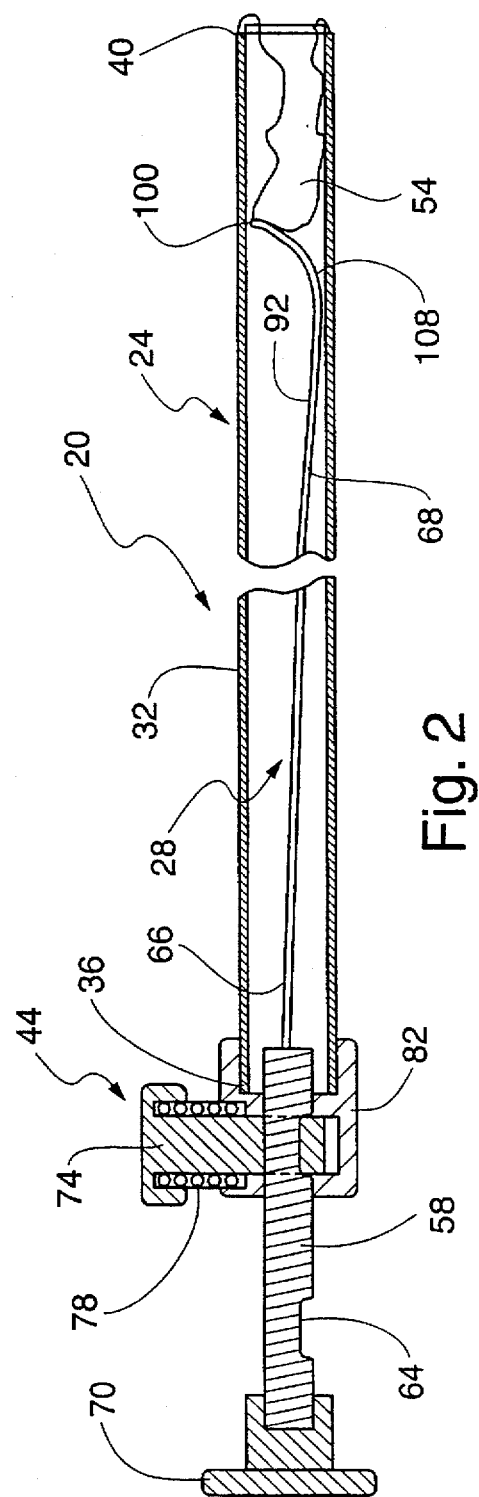
Fig. 3
Fig. 2

SURGICAL RETRACTOR

FIELD OF THE INVENTION

The present invention relates to a medical apparatus for assisting the surgeon in performing a surgical procedure and, in particular, to a retractor assembly for moving and holding a great-in-size body vessel in a desired location during the surgical procedure.

BACKGROUND OF THE INVENTION

Numerous medical operations require use of retractor devices that engage and manipulate body vessels in order to eliminate them as an obstruction or an interference during the operation. Movement of the body vessel or vessels away from the operation area is also intended to safeguard the vessel or vessels from unwanted contact or damage during the operation.

A particular medical procedure that requires body vessel retraction is an anterior spinal fusion procedure. This medical procedure is performed when intractable low back pain exists and non-operative treatments have proven to be unsatisfactory. The common cause for such intractable low back pain relates to a disc that is failing to function as a satisfactory shock absorber with resultant disc space collapse and with narrowing of the intervertebral space. The space that is available for exiting nerve roots also diminishes. Other causes for the intractable pain can relate to instability of the spine.

Anterior surgical procedures have significant advantage, in comparison with posterior procedures, in terms of time of recovery, morbidity of the operation and length of hospitalization. These attributes are realized because abdominal surgery for spine fusion tends to be a less invasive process than the posterior procedures due to decreased blood loss, decreased risk of infection and markedly less destructive approach to the spine. Anterior procedures also have the advantage of applying spinal fixation techniques which do not employ temporary internal splints, such as the case with posterior procedures which typically involve pedicle screws and rods. In the typical posterior spinal fusion, there is about a 30% chance that the posterior instrumentation will need to be removed within one year of implantation.

Patients undergoing the anterior spinal procedure can have the operation performed using a variety of different spinal fusion cages. These are devices placed within the disc space after thorough debridement of the area which allow for interbody fusion to take place using the patient's own bone packed into the fusion cage. The cage tends to distract the disc space to a point of original disk height thereby allowing increased space for neural exit from the spinal canal and restoration of the normal contour of the spine. In most instances, anterior cage fusions are confined to one or two level spine fusions, while procedures that involve arthrodesis or fusion of more levels require posterior segmental instrumentation, as well as an anterior fusion in order to increase the likelihood of fusion and increase the structural stability of the construct.

Selected patients with certain conditions have an option of a laparoscopic approach to the lumbar spine when their disease process is confined to the L5-S1 level of the spine. This procedure involves a general anesthetic for the patient and then placement of a laparoscopic portal beneath the umbilicus. The abdomen is then insufflated with carbon dioxide, thereby allowing an increase in the potential space available for the abdominal contents. The patient is then placed in the Trendelenburg position which allows the abdominal contents to fall towards the diaphragm and away from the lower portion of the spine where the operation is to take place. A laparoscope is then placed within the patient's abdominal cavity and exploration is carried out to make certain that there are no adhesions between an intestine and abdominal wall or between abdominal viscera and the L5-S1 area. Once clear visualization of the abdominal cavity has taken place, sites for additional portals in the lower quadrants of the abdomen are identified and it is through these portals that exposure of the L5-S1 interval is carried out. This involves tying off the median sacral blood vessels that tend to course directly over the L5-S1 interval. It also involves freeing up and mobilizing the iliac vessels as they traverse along the side of the L5-S1 disc. Once this process has been completed, it is then necessary to provide retraction of the great-in-size or diameter vessels so that they are out of the way of sharp reaming and disc preparation devices which are inserted through a separate portal above the pubis bone. These great vessels are typically 1 to 2 cm in size. The most serious and grave complications of anterior spinal fusions relate to injury to these great vessels. If the great vessels are injured during the course of the procedure, it necessitates emergency laparotomy or opening the abdomen in order to repair the vessels. There is potential for large volume blood loss and injury to the blood supply to the extremity and possible death of the patient. It is clear that great vessel retraction is mandatory in order to perform the procedure safely.

The currently available retractor for movement of the great vessels during an anterior spinal fusion procedure is identified as a laparoscopic peanut elevator. This device resembles a pencil with an eraser on the tip and it is the eraser tip that is used to help move the vessel away from the surgical area. This prior art device offers retraction only as wide as the device itself, which is typically 5 mm. This prior art retractor has certain drawbacks. It allows bulging of the great vessel around its edges and can allow vessel tissue to escape beneath it as well. Furthermore, such a prior art retractor may not allow for adequate visualization of the disc and the great vessels during performance of the medical procedure.

Because of these drawbacks associated with the currently utilized retractor, it would be advantageous to provide a retractor assembly that is sufficiently strong to eliminate unwanted bulging while making sure that the retractor assembly does not constitute a source of visual interference or obstruction.

SUMMARY OF THE INVENTION

In accordance with the present invention, a medical retractor apparatus is provided, particularly for use in moving great-in-size or diameter body vessels when a surgical procedure is to be performed. Such great vessels are typically in the range of 1 cm–2 cm in diameter and the lengths of such great vessels can extend upwards of several centimeters. It is necessary that such a retractor apparatus be positioned through a relatively small sized portal in the patient and yet have the strength and sufficient lateral extent for controlling movement of these great vessels.

The medical retractor apparatus includes a housing assembly and a retractor assembly operatively joined thereto. The housing assembly has a retractor body and a latch mechanism used in controlling the retractor assembly. The retractor assembly includes a retractor element having a tip that has a retracted position and an extended position. The retracted position refers to at least major portions of the retractor element being held within the retractor body. The extended position refers to such portions being disposed outwardly of the retractor body and with the retractor element tip being fully extended in a lateral or width-wise direction.

The retractor body also has a proximal end, which is opposite the distal end. The retractor element extends from the proximal end when in use. The proximal end is preferably circular and has a diameter of about 10 mm or less. The relatively small diameter or width enables the retractor body to be inserted through a relatively small portal in the patient. However, when the retractor element is in its extended position, it has a lateral extent or width substantially greater than the proximal end width. Preferably, the tip of the retractor element has a width at least greater than about 15 mm and, preferably, about 20 mm. The proximal end can also be defined as including a center, with a top area including a top point and a bottom area or bottom point, which is at the same distance as the top point from the proximal end center. When exiting the proximal end to assume its extended position, the retractor element is offset from the proximal end center. The offset is towards the top area of the proximal end. When in the extended position, the retractor element tip is closer to the bottom area than to the top area of the proximal end. This relative positioning optimizes visualization of the surgical area by the surgeon without interference from or obstruction by the retractor element. The proximal end also preferably has a confining or locking member. In one embodiment, the confining member includes at least one groove that confines the retractor element and does not allow unwanted rotating or turning movements of the retractor element that might occur during contact with the great vessel that is being manipulated by the retractor element.

In one embodiment, when the retractor element is extended, it includes at least a first loop having a bend. The bend is closer to the mid-portion of the first loop than it is to the proximal end of the retractor body. The bend results in the first loop being comprised of two loop portions. The bend and loop portions enhance desired contact and movement of the particular great body vessel. In another embodiment, the retractor element includes two spaced apart first and second loops, with the apex of each loop being located substantially at opposite ends of the retractor element tip. A cover member or pouch can be included with each of the single loop and double loop embodiments. The cover member surrounds all portions of the retractor element in its extended position and comes in contact with the great vessel when the retractor element is used to engage it.

In addition to the expanded lateral extent of the retractor element in its extended position, it is very important that the retractor element have sufficient strength for controlling and maintaining the position of the great vessel. For this to be properly achieved, the retractor element must be made of a material and/or have a size that provides a tensile strength in the range of about 0.2–0.65 lbs. Likewise, the retractor element must have a compression strength in the range of about 0.2–0.5 lbs.

With respect to use of the medical apparatus of the present invention, after the necessary portals have been made, the medical apparatus of the present invention is inserted through a portal located to permit access to a great vessel that must be moved away from the surgical area at which a surgical procedure is to be performed, such as an anterior spinal fusion procedure. During the insertion, the retractor element is in its retracted position. Once properly positioned, the latch mechanism is activated to allow the retractor element to assume its extended position. The retractor element is maneuvered to firmly engage the great vessel. After sufficient movement away from the surgical area, the retractor element is maintained in that position and holds the great vessel so that it does not interfere with the surgical procedure to be performed. In that regard, because of the extent and strength of the retractor element, the great vessel is maintained in back of and away from the surgical area at which the surgical procedure is to be performed. Accordingly, even those portions of the great vessel adjacent to the retractor element do not improperly bulge out towards the surgical area. Quantitatively speaking, those portions of the great vessel not directly contacted by the retractor element, but adjacent thereto and which extend at least 4 cm from the edge of the retractor element, do not bulge in a direction towards the surgical area. That is, a straight line defined as passing through all portions of the retractor element tip and continuing or extending past the tip for at least 4 cm defines a boundary behind which such great vessel portions are held. Further, due to the strength of the retractor element, it can be compressed against other body parts or tissue in connection with manipulating the retractor element for properly engaging the great vessel. Such compression of the retractor element is achieved without any loss of necessary shape or functionality.

Based on the foregoing summary, a number of important advantages of the present invention are readily seen. A medical retractor apparatus is provided that includes a retractor element that has a retracted position and an extended position. The retracted position enables the retractor element to be inserted through a relatively small sized portal formed in the patient. The extended position enables the retractor element to engage and manipulate a great vessel away from a surgical area and hold it in place during the particular surgical procedure, such as an anterior spinal fusion. The retractor element exits the proximal end of the retractor body offset from the center to optimize avoidance of great vessel interference during the surgical procedure. The retractor element is essentially locked in place in its extended position to prevent unwanted turning of the retractor element during movement of the great vessel. A bend is formed in the retractor element to facilitate suitable engagement and holding of the great vessel. The retractor element is also configured in a shape and made with a material that eliminates unwanted bulging of the great vessel in a direction towards the surgical area.

Additional advantages of the present invention will become readily apparent from the following discussion, particularly when taken together with the accompanying drawings.

BRIEF DESCRIPTION OF THE DRAWINGS

FIG. 1 is a perspective view of the medical retractor apparatus with retractor element in its extended position;

FIG. 2 is a longitudinal cross-sectional view illustrating the apparatus with the retractor element in its extended position;

FIG. 3 is a longitudinal cross-sectional view of the apparatus with the retractor element in its retracted position;

DETAILED DESCRIPTION

Figure 6:
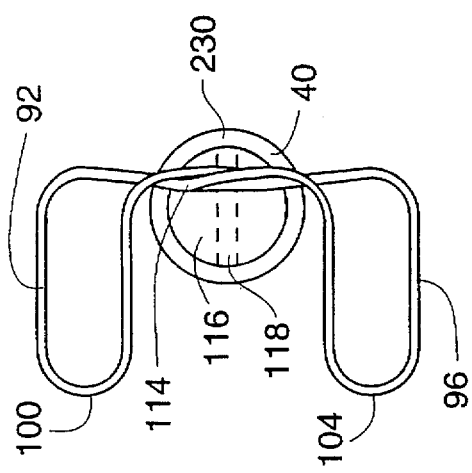
FIG. 6 is an enlarged end view of the retractor element in its extended position without the cover member.

With reference to FIG. 1, a medical retractor apparatus 20 is disclosed. The retractor apparatus 20 is used in moving, holding or otherwise positioning body vessels, particularly great-in-size body vessels. Such body vessels are commonly 1 cm in diameter and greater. Positioning of such body vessels is important as part of performing surgical procedures on patients, for example during anterior spinal fusions. A representative example of such a surgical procedure utilizing the retractor apparatus 20 will be described later herein.

The retractor apparatus 20 includes a housing assembly 24 and a retractor assembly 28. The retractor assembly 28 engages the great vessel when positioning it away from the body area at which the surgical procedure is to be performed. As part of that positioning, the retractor assembly 28 holds the body vessel in place while the procedure is being performed.

The housing assembly 24 includes a retractor body 32 that is generally cylindrically shaped and is elongated for extending through a portal in the patient's skin. Preferably, the diameter or width of the retractor body 32 is no greater than about 10 mm so that only a relatively small sized portal need be made which can properly receive the elongated retractor body 32. The retractor body has a distal end 36 and a proximal end 40, with the proximal end 40 being the end of the retractor body 32 that is positioned adjacent the body vessel that is to be moved. The distal end 36 is the opposite end of the retractor body 32 and is connected to a latch mechanism 44. The latch mechanism 44 controls movement of the retractor assembly 28 relative to the retractor body 32.

With reference to FIGS. 2 and 3 also, the retractor assembly 28 has two states or positions. FIG. 2 illustrates a retracted position in which all or substantially all portions of the retractor assembly 28 are contained within the retractor body 32. FIG. 3 shows the other or extended position of the retractor assembly 28 in which a retractor element 50 extends from the proximal end 40 in a position for engaging and manipulating a body vessel. In the illustrated embodiment, the retractor element 50 is surrounded by a cover member or pouch 54 when the retractor element 50 is in the extended position. Although the retractor assembly 28 need not include the cover member 54, it can be beneficial in providing an appropriate contacting surface for the body vessel to be moved. Preferably, when the cover member 54 is utilized, it also has a retracted position (FIG. 2) and an extended position (FIG. 3).

As seen in FIGS. 2 and 3, the latch mechanism 44 includes a slide member 58 connected to the retractor assembly 28, namely, an actuator rod 66 that extends a substantial distance, at least half the length of the retractor body 32. The retractor element 50 is coupled to the actuator rod 66 using some form of connector 68, as diagrammatically illustrated in FIGS. 2 and 3, although a more detailed embodiment related to the construction of the retractor element and its connection to the actuator rod 66 will be later described in conjunction with FIGS. 4–6. At its opposite end, the slide member 58 has a knob 70 joined thereto for engagement by the surgeon or operator of the retractor apparatus 20. A spring 78 is located about the periphery of portions of a release member 74. The spring 78 is biased to maintain the release member 74 in an upward position. A sleeve 82 surrounds the distal end 36 of the retractor body 32. In association with the two positions of the retractor assembly 28, the slide member 58 also has two positions. As seen in FIG. 2, a first notch 62 of the slide member 58 is held by the release member 74. In so doing, the retractor assembly 28 is in its retracted position. As seen in FIG. 3, the release member 74 holds the slide member 58 in place using a second notch 64 when the retractor assembly is in its extended position. Movement of the slide member 58 and between the first and second notches 62, 64 is achieved by depressing the release member 74 against the force of the spring 78. In conjunction with movement of the slide member from the position of FIG. 3 to the position of FIG. 2, the knob 70 is pulled outward by the practitioner as the release member 74 is pushed inward relative to the sleeve 82.

Figure 4:
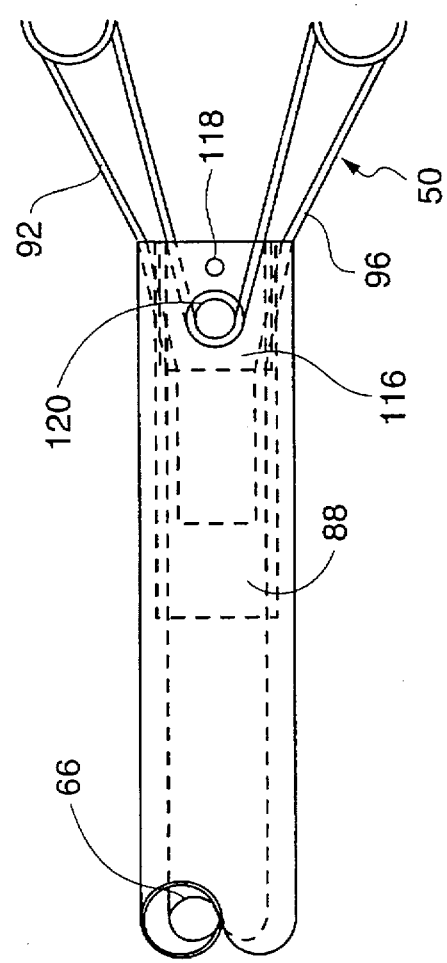
FIG. 4 is an enlarged, fragmentary, longitudinal top section illustrating the retractor element in its extended position and without a cover member about the retractor element.
Figure 5:
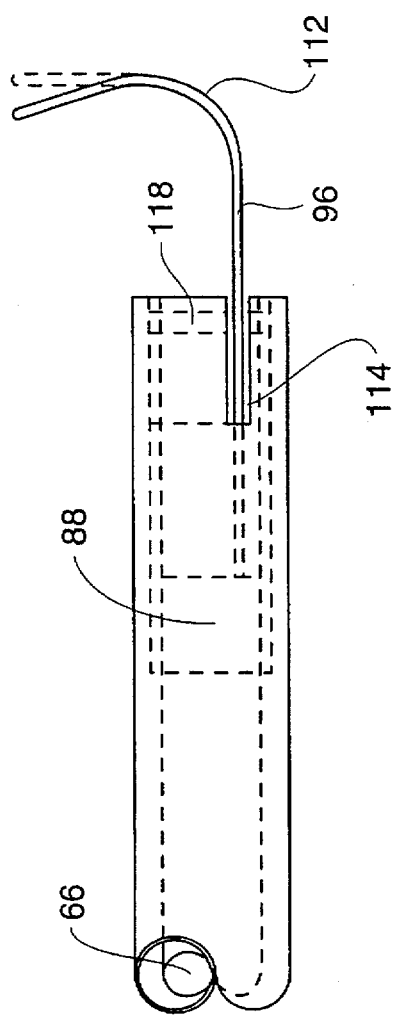
FIG. 5 is an enlarged, fragmentary, longitudinal side section of the retractor element in its extended position without the cover member.

With reference to FIGS. 4–6, the retractor assembly 28, particularly the retractor element 50, is next described in greater detail. The retractor assembly 28 also includes a retractor clamp 88 to which the actuator rod 66 is connected at its end opposite from the end connected to the slide member 58. Also attached to the actuator clamp 88 is the retractor element 50 that, in the preferred embodiment, is made from a single wire or piece. As also seen in FIG. 1, the retractor element 50, in the illustrated embodiment, includes first and second loops 92, 96. The two loops 92, 96 are spaced from each other and include tips 100, 104, respectively. The first loop 92 also has a bend 108 and the second loop has a bend 112. Before the bends 108, 112, each of the loops 92, 96 is substantially parallel to or extend along the axis of the retractor body 32. After the bends 108, 112, these loops 92, 96, respectively, have portions that extend back towards the retractor body 32. Preferably, each of the bends 108, 112 is located more adjacent the midportions of their respective loops 92, 96 than to the proximal end 40 of the retractor body 32. Such a bending configuration is advantageous in grasping and moving the great body vessels that are intended to be positioned by the retractor apparatus 20.

When the cover member 54 is part of the embodiment, the tips 100, 104 of the first and second loops, 92, 94, respectively, are disposed adjacent to opposite ends of the cover member 54. Additionally, the first and second loops 92, 96 are of a size such that intermediate portions of the cover member 54 are located between the two loops 92, 96.

With regard to forming the first and second loops 92, 96, from the single wire, as best seen in FIG. 4, one end of the retractor element 50 is attached to the actuator clamp 88 and extends for a short distance within the retractor body 32. The retractor element 50 exits the proximal end 40 of the retractor body, when the retractor element 50 is in its extended position, through a slot 114 formed in a guide member 116. The slot 114 is used in confining movement of the retractor element 50, as will be further discussed later herein. The guide member 116 has two semi-circular shaped portions that are interconnected using a guide bar 118. Exiting of the wire of the retractor element 50 from the slot 114 and the proximal end 40 results in the first loop 92 being formed, which includes the bend 108 and the tip 100. From the tip 100 of the first loop 92, the single wire of the retractor element 50 enters the proximal end 40, through the slot 114 and wraps around a retractor pin 120 (FIG. 4). The single wire of the retractor element 50 continues from the retractor pin 120 and again exits the slot 114 and the proximal end 40 to form the second loop 96 having the bend 112 and the tip 104. From the tip 104 of the second loop 96, the single wire again enters the proximal end 40, the slot 114 and passes the same short distance into the retractor body 32 and is attached to the actuator clamp 88.

Important to the present invention is that the single piece of wire be made from a material that has memory whereby the retractor element 50 can be disposed within the retractor body 32 in its retracted position; however, when disposed in its extended position, the retractor element "remembers" to form the first and second loops 92, 96. As should also be appreciated, the single wire could also be formed into a single loop, which may be surrounded by the cover member 54, or may be exposed for engaging a great body vessel.

Figure 7:
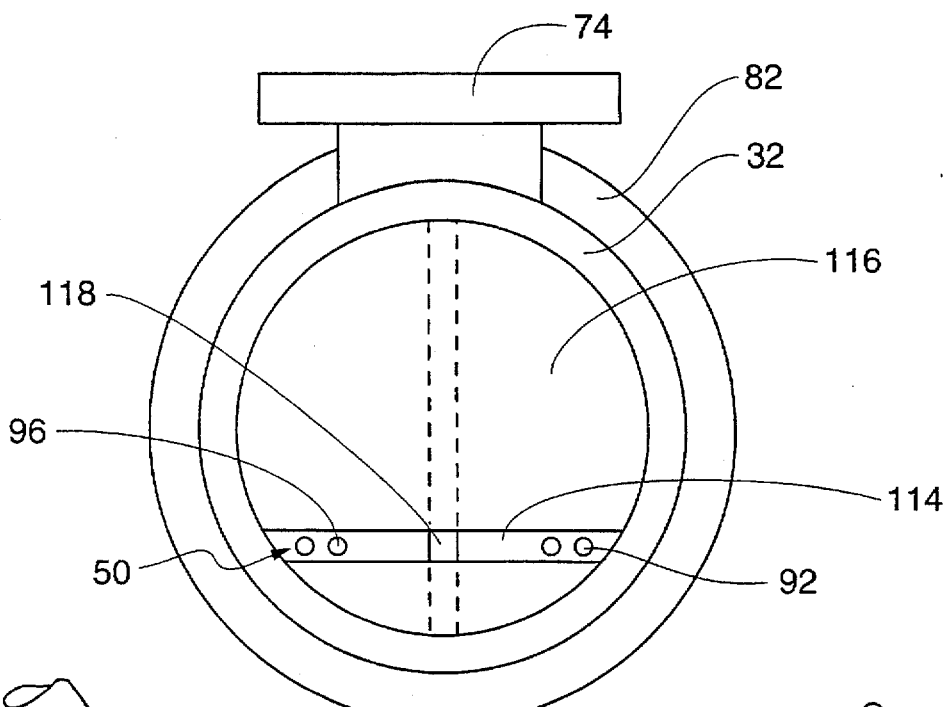
FIG. 7 is an enlarged, fragmentary cross-sectional end view of the retractor element that shows parts of the retractor element exiting the proximal end of the retractor body offset from the center of the proximal end and the slot at the proximal end for preventing unacceptable turning of the retractor element.

With reference to FIG. 7, a further description of the slot 114 or the retractor element 50 confining structure 24 is provided. In particular, at the proximal end 40 of the retractor body 32, a guide member 116 is held that includes the slot 114. The slot 114 receives and holds portions of the first loop 92 and portions of the second loop 96. When the retractor element 50 is in its extended position for engaging a great body vessel, the slot 114 and the walls of the guide member 116 act to prevent unwanted turning or rotational movement of the retractor element 50. That is, when the retractor element 50 is contacting and moving a great vessel, a tendency arises for the retractor element to twist or turn. This is undesirable in utilizing the retractor apparatus 20. To alleviate this possibility, the extended retractor element 50 has portions thereof held by the slot 114. Consequently, when a twisting force is applied to the retractor element 50, it is resisted by the locking or confining of such portions of the retractor element 50 in the slot 114 and, particularly, resisted by the inner walls of the guide member 116 that define the slot 114.

Figure 8:
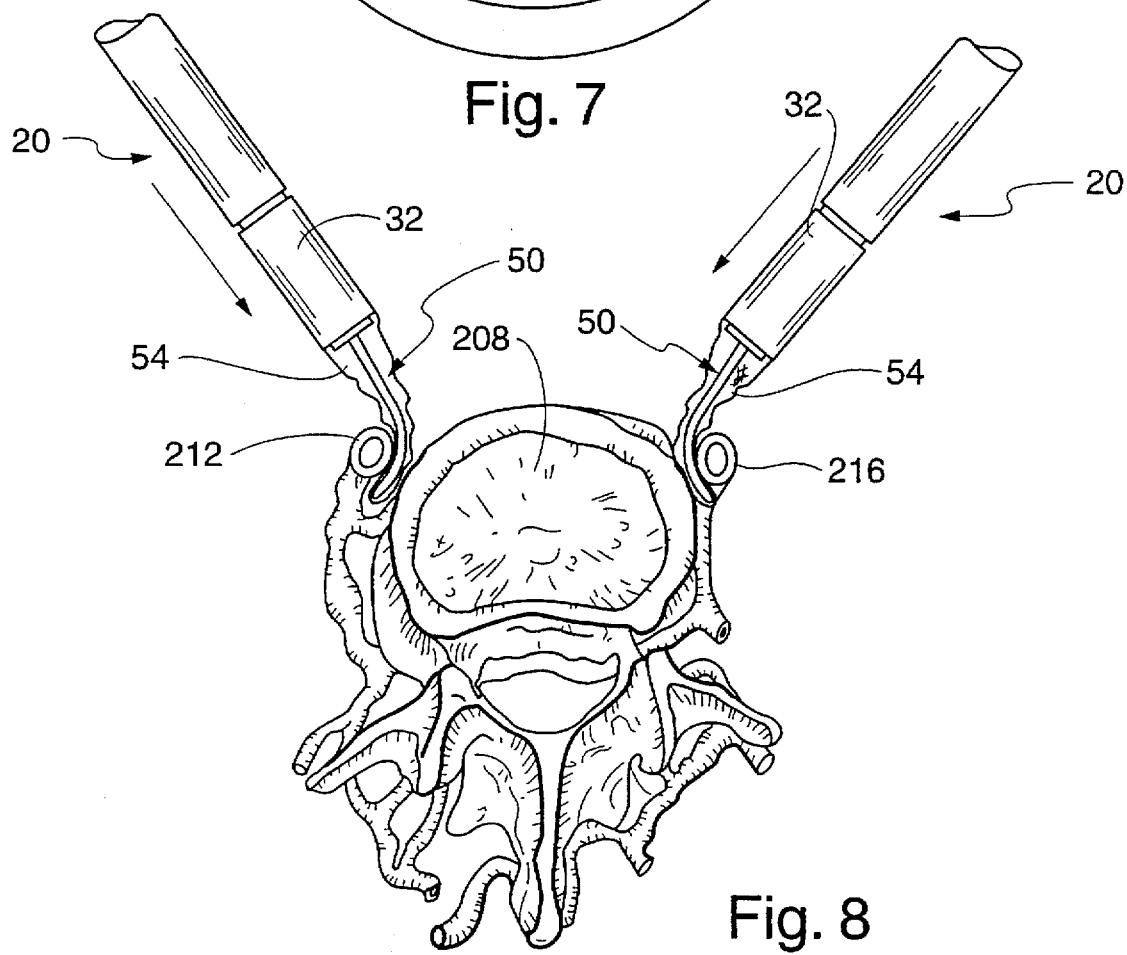
FIG. 8 is a schematic frontal view illustrating use of the retractor apparatus in positioning a great vessel during an anterior spinal fusion procedure.
Figure 9:
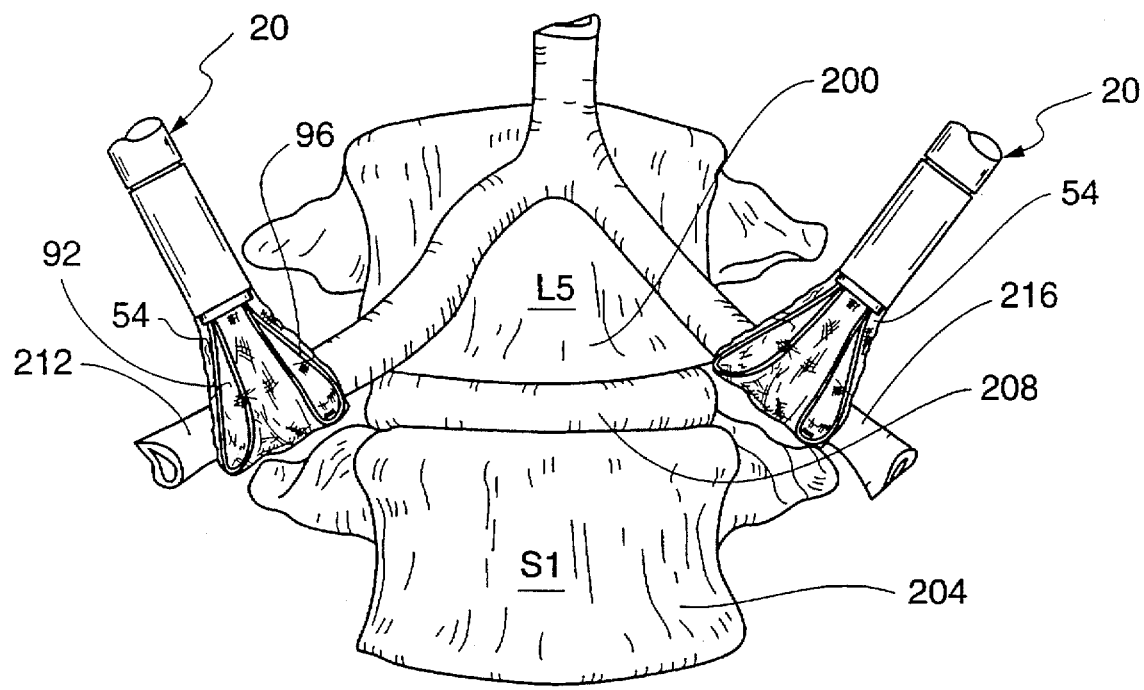
FIG. 9 is a schematic sectional view further illustrating use of the retractor apparatus in holding a great vessel in position away from the surgical area.
Figure 10:
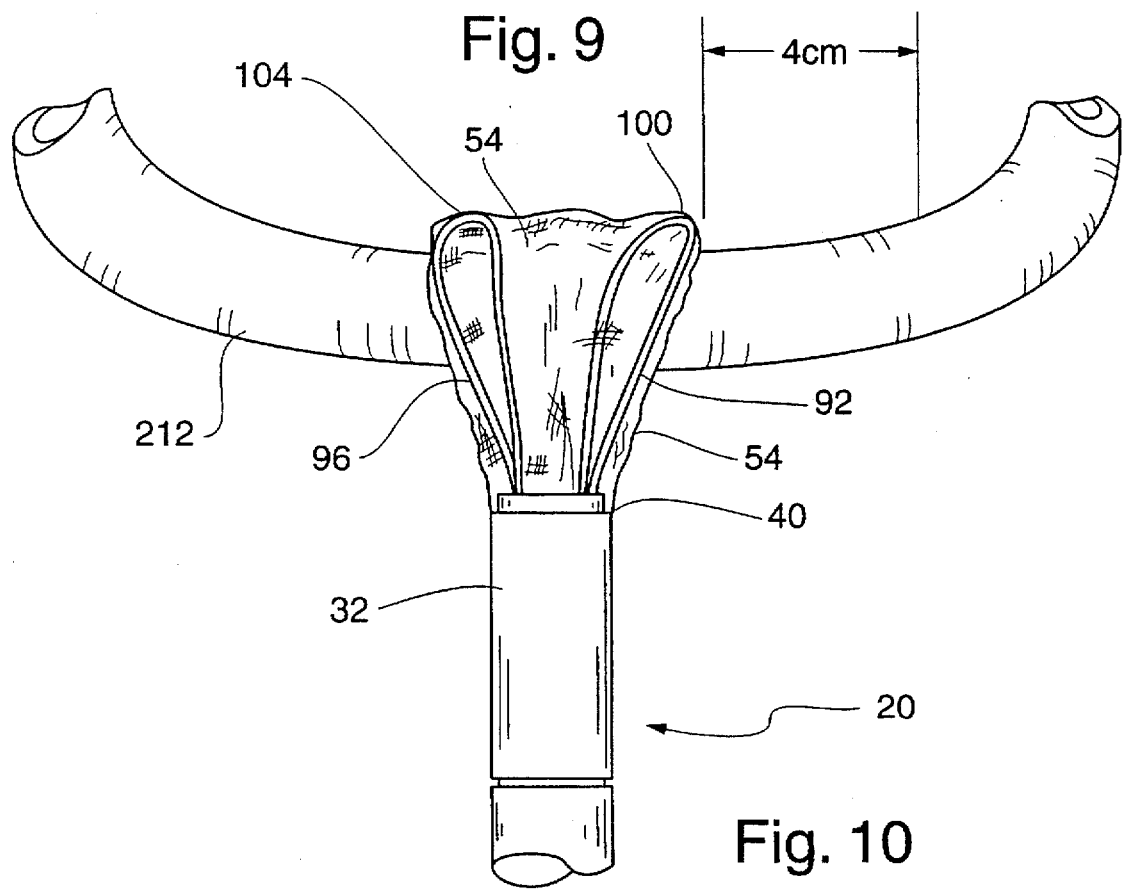
FIG. 10 schematically illustrates prevention of unwanted bulging of the great vessel as part of maintaining the great vessel at a sufficient distance from the surgical area.

The medical retractor apparatus 20 is suited for a number of surgical procedures that require movement and positioning of body vessels, particularly where the vessels are great-in-size, such as at least 1 cm in diameter and usually 2 cm or greater in diameter. A representative medical procedure that employs the retractor apparatus 20 is an anterior spinal fusion. With reference to FIGS. 8–10, utilization of the retractor apparatus 20 in such a representative medical procedure is next described.

Briefly, a representative medical procedure involves surgery at the L5-S1 level of the patient's spine. As seen in FIGS. 8 and 9, the L5-S1 level includes an L5 vertebral body 200, an S1 vertebral body 204, and a disc 208 disposed therebetween. The anterior spinal operation involves placing one or more spinal fusion cages at spaces occupied by the disk 208. In that regard, a sharp reaming, or other disc preparation, device is employed in order to provide one or more openings in the disc for such cages. However, in order to perform such reaming of the disc 208, it is necessary that certain body vessels be moved from their usual position adjacent to and in front of the surgical area or site. In particular, iliac body vessels 212, 216 essentially block the surgical area and need to be moved and held away from the surgical area that involves reaming of the disc 208. These iliac vessels 212, 216 are great-in-size body vessels of at least 1 cm in diameter.

In order to properly position the iliac vessels 212, 216 away from the surgical area, two medical retractor apparatuses 20 are employed simultaneously. Two symmetrically located portals are created through the patient's skin of a relatively small size to receive the retractor body 32, with the retractor element 50 in its retracted position (inside the retractor body 32). As previously noted, the retractor body 32 has a diameter of about 10 mm or less. A laparoscopic instrument or the like is utilized by the surgeon to identify these two iliac vessels 212, 216. At an appropriate time after insertion of the retractor body 32, the latch mechanism 44 is deployed to cause the retractor element 50 to be in its extended position. More specifically, the surgeon pushes on the release body 74 so that it is moved towards the sleeve 82 thereby releasing the slide member 58 and enabling it to move in a direction towards the proximal end 40 of the retractor body 32, when the surgeon pushes on or applies a force to the knob 70. This results in the retractor element 50 assuming the shape previously described including the first and second loops 92, 96, with their respective bends 108, 112 whereby the tips 100, 104 are disposed rearward in a direction towards the proximal end 40.

Once the retractor element 50 is in its extended position, it can be used to contact and move an iliac vessel 212, 216. Assume that the retractor apparatus 20 is positioned to move the iliac vessel 212. With reference to FIG. 8, it may be necessary or appropriate for the retractor element 50 to engage one of the vertebral members, such as the L5 vertebral body 200, S1 vertebral body 204, and/or disc 208. In doing so, the retractor element 50 may be compressed against one or more of these vertebral members in order to best grasp or grab hold of the iliac vessel 212. Such a compression of the retractor element 50 enables it to slide or otherwise move beneath the iliac vessel 212 to secure the engagement between the retractor element 50 and the first iliac vessel 212.

It is important that the wire from which the first and second loops 92, 96 are formed have sufficient compressive strength to enable the retractor element 50 to perform this manipulation without loss of shape or strength of the first and second loops 92, 96 including their bent portions. The wire and the resulting first and second loops 92, 96 must have a compression strength in the range of about 0.2–0.5 lbs.

Once the retractor element 50 has solid engagement with the first iliac vessel 212, the surgeon can then cause movement of the first iliac vessel 212 by pulling back on the retractor apparatus 20 adjacent to the distal end 36, such as by pulling adjacent to the latch mechanism 44. The iliac vessel 212 is moved until it is at a sufficient distance away from the surgical area, as can be determined by the surgeon using the laparoscopic instrument. Once in this desired position, the retractor apparatus 20 is held in place thereby holding the first iliac vessel 212 in an acceptable position so that the surgical operation can be performed at the surgical area without interference therefrom.

With the first iliac vessel 212 in this position away from the surgical area, two further important features are next described that are based on the structure or design of the retractor apparatus 20, particularly the retractor element 50. First, with reference also to FIG. 5, the retractor element 50, particularly the first and second loops 92, 96 thereof, exit the proximal end 40 in such a way as to optimize or reduce potential visual interference, while not moving the iliac vessels 212, 216 any greater distance than is necessary. In particular, the retractor element 50 exits the proximal end 40 offset from the center thereof. This offset is in a direction of the proximal end 40 opposite from the bent tips 100, 104. Consequently, there is relatively less chance for the proximal end 40 to obstruct or possibly interfere during the surgical procedure. This is in contrast with a retractor element 50 that exits the proximal end 40 such that more of the proximal end 40 extends beyond or outwardly relative to the retractor element 50. Stated another way and referring to FIG. 5, the proximal end 40 includes an apex 230 adjacent to which the retractor element 50 exits. Due to this positioning of the retractor element 50 relative to this portion or apex 230 of the proximal end 40, less visual interference by the retractor body 32 is achieved.

The second feature relates to the strength and lateral extent of the retractor element 50, particularly when holding the great vessel in place during the surgical procedure. With particular reference to FIG. 10, the width or lateral extent of the retractor element 50, especially that lateral extent established between the tips 100, 104, is greater than the diameter or width of the retractor body 32. This lateral extent is at least 15 mm and preferably 20 mm or greater. Such lateral extent enables the retractor element 50 to contact or otherwise engage more portions of a great vessel. This provides significant control and stability in connection with grasping, moving and holding the great vessel. The first and second loops 92, 96 also must have a sufficient tensile strength to hold such great vessels in place away from the surgical area, as well as sufficient strength to move the great vessel to its proper position. This tensile strength is in the range of about 0.2–0.6 lbs. Having such a tensile strength enables the retractor element 50 to satisfactorily position the great vessel without loss of its desired shape for firmly engaging the great vessel. Relatedly, the lateral extent and tensile strength associated with the retractor element 50 eliminates or avoids unwanted bulging of portions of the great vessel. That is, the dimensions and strength of the retractor element 50 maintain portions of the great vessel that are adjacent to opposite edges of the retractor element 50 from extending into the surgical area. Because there is no such unwanted bulging, there is no visual interference due to these adjacent portions of the great vessels. As illustrated in FIG. 10, the retractor element 50 avoids bulging of such adjacent portions of a great vessel in a distance of at least about 4 cm. Specifically, a straight line that is drawn through the tips 100, 104 of the first and second loops 92, 96 respectively, extends for at least an additional about 4 cm from the opposing edges of the retractor element 50 before the great vessel extends back in a direction towards the surgical area. Hence, bulging of the great vessel towards the surgical area immediately adjacent to the retractor element 50 is eliminated.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described hereinabove are further intended to explain the best mode presently known of practicing the invention and to enable others skilled in the art to utilize the invention as such, or in other embodiments, and with the various modifications required by the particular application or uses of the invention. It is intended that the appended claims be construed to include alternative embodiments to the extent permitted by the prior art.

What is claimed is:

1. A medical apparatus for use in controlling position of a great-in-size body vessel relative to a surgical area during a surgical procedure, comprising:

a housing assembly including a retractor body that has a proximal end for positioning adjacent the body vessel and a distal end, said proximal end having a width, a center, a first area and a second area opposite said first area and in which said housing assembly further includes a latch mechanism joined to said retractor body; and a retractor assembly including a retractor element having a tip and including at least a first loop having a tip and said first loop tip being part of said retractor element tip, said retractor element including a retracted position and an extended position in which said retractor element tip has a width greater than said width of said proximal end, said retractor element being in said extended position when said latch mechanism is in a first state, said retractor assembly further including a guide member having a slot positioned in said retractor body, said guide member being closer to said proximal end than said latch mechanism, said slot being offset from said center of said proximal end, said first loop having a bend, with said slot being closer to said first area than to said second area and said first loop tip being in a direction towards said second area based on said first loop bend when said retractor element is in said extended position.

2. A medical apparatus, as claimed in claim 1, wherein: said first loop bend separates said first loop into first and second loop portions, said first loop bend being more adjacent a middle of said first loop than said proximal end of said retractor body.

3. A medical apparatus, as claimed in claim 1, wherein: said slot being of dimensions through which said retractor element passes to attain each of said retracted and extended positions, wherein portions of said retractor element in said slot contact said guide member during a turning movement of said retractor element to thereby limit said movement.

4. A medical apparatus, as claimed in claim 1, wherein: said retractor element further includes a second loop and in which said first and second loops are spaced from each other at opposite ends of said retractor element tip and in which said proximal end has an internal diameter less than about 10 mm and said width of said retractor element tip in said extended position is in the range of about 15–25 mm.

5. A medical apparatus, as claimed in claim 4, wherein: said retractor element includes a cover member surrounding at least said retractor element tip and with said cover member being made of a material that enables said cover member to support portions of the great-in-size body vessel.

6. A medical apparatus, as claimed in claim 1, wherein: said retractor element has a tensile strength in the range of about 0.2–0.65 lbs.

7. A medical apparatus, as claimed in claim 6, wherein: said retractor element has a compression strength in the range of about 0.2–0.5 lbs.

8. A medical apparatus for use in controlling position of a great-in-size body vessel, comprising:

a housing assembly including a retractor body having a length and a proximal end with a center and a width, said housing assembly further including a latch mechanism joined to said retractor body; and a retractor assembly including a retractor element having a tip with a width, said retractor element having a retracted position and an extended position in which said retractor element tip has a maximum width that is greater than said width of said proximal end and in which said latch mechanism has a first state for enabling said retractor element to be in said extended position, and wherein said retractor assembly has a guide member in said retractor body with a slot formed by inner walls of said guide member through which said retractor element passes to attain each of said retracted and extended positions and wherein all portions of said retractor element extend directly from said proximal end and all portions of said retractor element are prevented from extending outwardly from along said length of said retractor body when said retractor element is in said extended position.

9. A medical apparatus, as claimed in claim 8, wherein:

said retractor assembly includes a cover member surrounding outer portions of said retractor element when said retractor element tip has said maximum width.

10. A medical apparatus, as claimed in claim 8, wherein:

said retractor element includes first and second loops that are spaced from each other when said retractor element is in said extended position.

11. A medical apparatus, as claimed in claim 8, wherein:

said proximal end has a first area and a second area and said retractor element includes at least a first loop with a bend and having a tip, said slot being closer to said first area than said second area and said tip being closer to said second area than said first area when said retractor element is in said extended position.

12. A method for controlling movement of a great-in-size body vessel relative to a surgical area that is being accessed by a surgeon during a surgical procedure, comprising:

providing a medical apparatus that includes a housing assembly having a proximal end and a retractor assembly, said retractor assembly including a retractor element having a tip with an outer edge;

positioning said proximal end adjacent to the surgical area;

extending said retractor element such that said retractor element tip has a maximum width, with said maximum width being greater than said width of said proximal end;

contacting with said retractor element said great-in-size body vessel having a width of at least 1 cm, said contacting step including compressing at least portions of said retractor element and sliding said retractor element beneath said great-in-size body vessel to secure engagement between said great-in-size body vessel and said retractor element and in which said compressing step includes compressing said retractor element such that said retractor element is subject to at least about 0.2 lb. of force;

moving said great-in-size body vessel away from the surgical area using said retractor element; and holding said great-in-size body vessel away from the surgical area using said retractor element, wherein said holding step includes maintaining portions of said great-in-size body vessel that extend at least 4 cm from said outer edge of said retractor element tip away from the surgical area and wherein an extended straight line is defined that passes through all portions of said retractor element tip and past said outer edge of said tip for at least about 4 cm, said body vessel portions that extend at least about said 4 cm from said outer edge of said tip being located on one side of said extended straight line and the surgical area being located on an opposite side of said extended straight line, and at least one of said moving and holding steps includes exerting at least about 0.2 lb. of force on said great-in-size body vessel using said retractor element.

13. A method, as claimed in claim 12, wherein:

said extending step includes releasing a latch mechanism associated with said housing assembly to permit said retractor element tip to reach said maximum width.

14. A method, as claimed in claim 12, wherein:

said extending step includes confining portions of said retractor element using a guide member having a slot through which said retractor element moves in order to prevent unwanted turning movement of said retractor element.

15. A method, as claimed in claim 12, wherein:

said extending step includes exiting said retractor element tip from said proximal end more adjacent a top area of said proximal end than a center thereof using a guide member having a slot positioned within a retractor body of said retractor assembly.

16. A method, as claimed in claim 12, wherein:

said retractor element includes at least a first loop having a center and in which said extending step includes bending said first loop more adjacent said center thereof than said proximal end.

* * * * *